US008480565B2

(12) United States Patent
Kawata et al.

(10) Patent No.: US 8,480,565 B2
(45) Date of Patent: Jul. 9, 2013

(54) ENDOSCOPE CONTROL APPARATUS

(75) Inventors: Susumu Kawata, Hachioji (JP);
Susumu Hashimoto, Hachioji (JP);
Yasuo Komatsu, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1119 days.

(21) Appl. No.: 12/254,454

(22) Filed: Oct. 20, 2008

(65) Prior Publication Data
US 2009/0105540 A1 Apr. 23, 2009

(30) Foreign Application Priority Data

Oct. 23, 2007 (JP) ................................. 2007-275606

(51) Int. Cl.
*A61B 1/04* (2006.01)
(52) U.S. Cl.
USPC ......................................................... 600/112
(58) Field of Classification Search
USPC .................................................. 600/118, 112
See application file for complete search history.

(56) References Cited

U.S. PATENT DOCUMENTS

| 4,860,094 | A | 8/1989 | Hibino et al. | |
|---|---|---|---|---|
| 6,319,197 | B1 * | 11/2001 | Tsuji et al. | 600/132 |
| 6,348,035 | B1 | 2/2002 | Takami | |
| 6,937,269 | B2 | 8/2005 | Sugimoto et al. | |
| 2002/0013512 | A1 * | 1/2002 | Sendai et al. | 600/160 |
| 2004/0080612 | A1 | 4/2004 | Sugimoto | |
| 2008/0144241 | A1 * | 6/2008 | Crawley et al. | 361/56 |

FOREIGN PATENT DOCUMENTS

| JP | 6-61203 A | 8/1994 |
|---|---|---|
| JP | 6-245901 | 9/1994 |
| JP | 07184852 A * | 7/1995 |
| JP | 09-308606 | 12/1997 |
| JP | 2004-209283 A | 7/2004 |
| JP | 2004-236738 | 8/2004 |
| JP | 2007-209570 | 8/2007 |

OTHER PUBLICATIONS

Translation of JP Publication No. 2004-236738; Title: Processor for Electronic Endoscope; Inventor: Akai, Nobuyuki; Publication Date: Aug. 26, 2004.*

* cited by examiner

*Primary Examiner* — Clayton E Laballe
*Assistant Examiner* — Fang-Chi Chang
(74) *Attorney, Agent, or Firm* — Scully, Scott, Murphy & Presser, P.C.

(57) ABSTRACT

An endoscope control apparatus of the invention includes: a first connector receiving portion and a second connector receiving portion, to and from which an endoscope is attachable and detachable; a connection detection portion for detecting a connecting state of the endoscope in the first connector receiving portion and the second connector receiving portion and outputting a connection detection signal; a first patient circuit electrically connected to a post stage of the first connector receiving portion and connected also to a first reference potential point; and a second patient circuit electrically connected to a post stage of the second connector receiving portion, and connected also to a second reference potential point different from the first reference potential point.

5 Claims, 4 Drawing Sheets

US 8,480,565 B2

ENDOSCOPE CONTROL APPARATUS

This application claims benefit of Japanese Application No. 2007-275606 filed on Oct. 23, 2007, the contents of which are incorporated by this reference.

BACKGROUND OF THE INVENTION

1. Field of the Invention

The present invention relates to an endoscope control apparatus, and more particularly to an endoscope control apparatus including a plurality of patient circuits.

2. Description of Related Art

Endoscope systems including an endoscope and an endoscope control apparatus for controlling the endoscope have been conventionally widely used in medical field and industrial field, and the like. In addition, in medical field, for example, endoscope systems are used in observing or performing various treatments on a living tissue and the like.

As an apparatus equivalent to the above-described endoscope control apparatus, a processor for electronic endoscope is proposed, for example in Japanese Patent Application Laid-Open Publication No. 2004-236738, which is capable of connecting a plurality of kinds of endoscopes by including a plurality of connector receiving portions.

The processor for electronic endoscope disclosed in the Japanese Patent Application Laid-Open Publication No. 2004-236738 has a configuration in which circuits electrically connected to the plurality of connector receiving portions are connected to a common GND (reference potential point) and the circuits operates through a common power source control circuit.

SUMMARY OF THE INVENTION

An endoscope control apparatus according to the present invention includes: a first connector receiving portion and a second connector receiving portion, to and from which an endoscope is attachable and detachable; a connection detection portion for detecting a connecting state of the endoscope in the first connector receiving portion and the second connector receiving portion and outputting a connection detection signal; a first patient circuit electrically connected to a post stage of the first connector receiving portion and connected also to a first reference potential point; and a second patient circuit electrically connected to a post stage of the second connector receiving portion, and connected also to a second reference potential point different from the first reference potential point.

DETAILED DESCRIPTION OF PREFERRED EMBODIMENT

Hereinafter, an embodiment of the present invention will be described with reference to the drawings.

Figure 1:
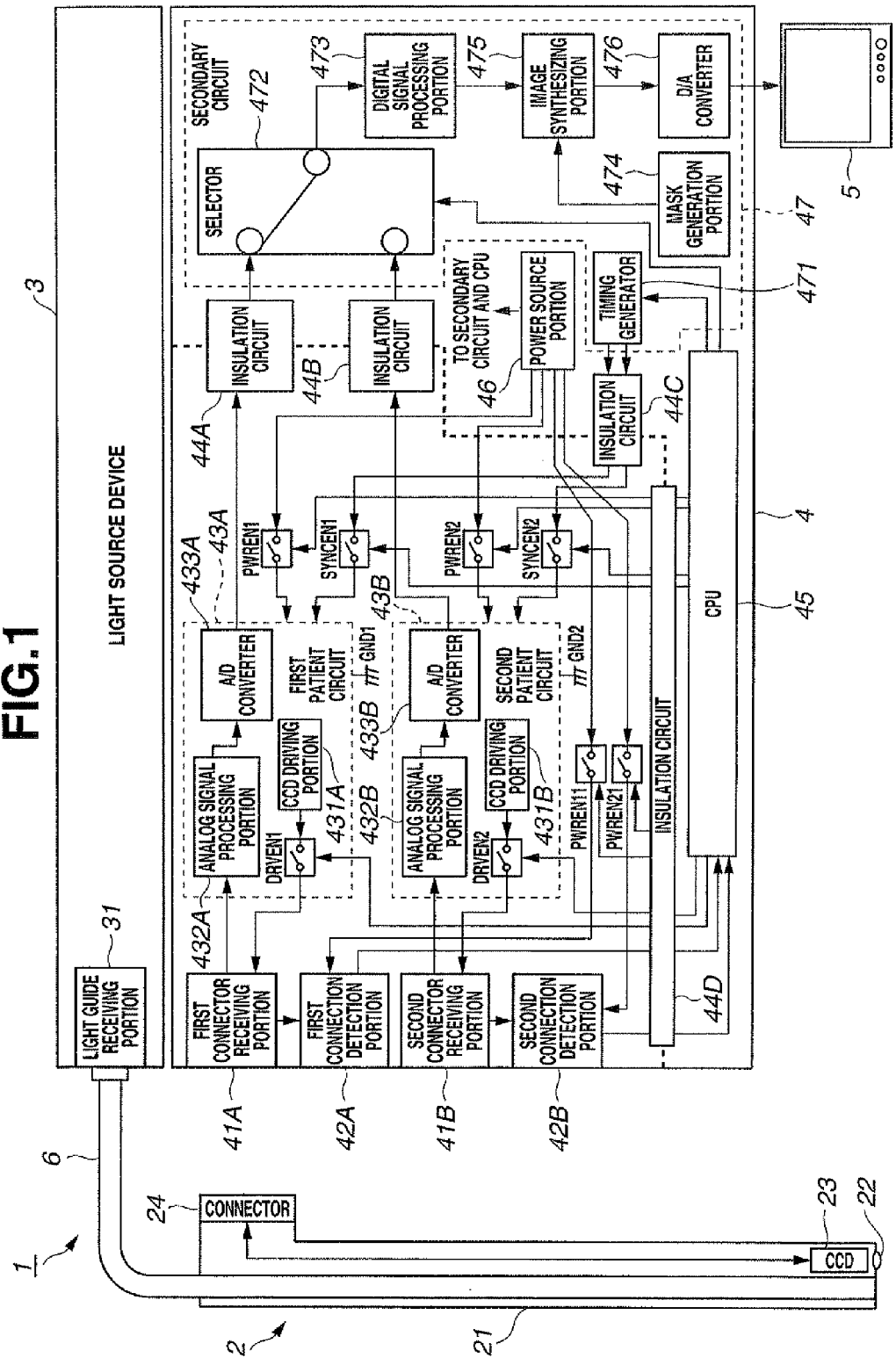
FIG. 1 is a view showing an example of a configuration of an endoscope system provided with a processor according to an embodiment of the present invention.
Figure 2:
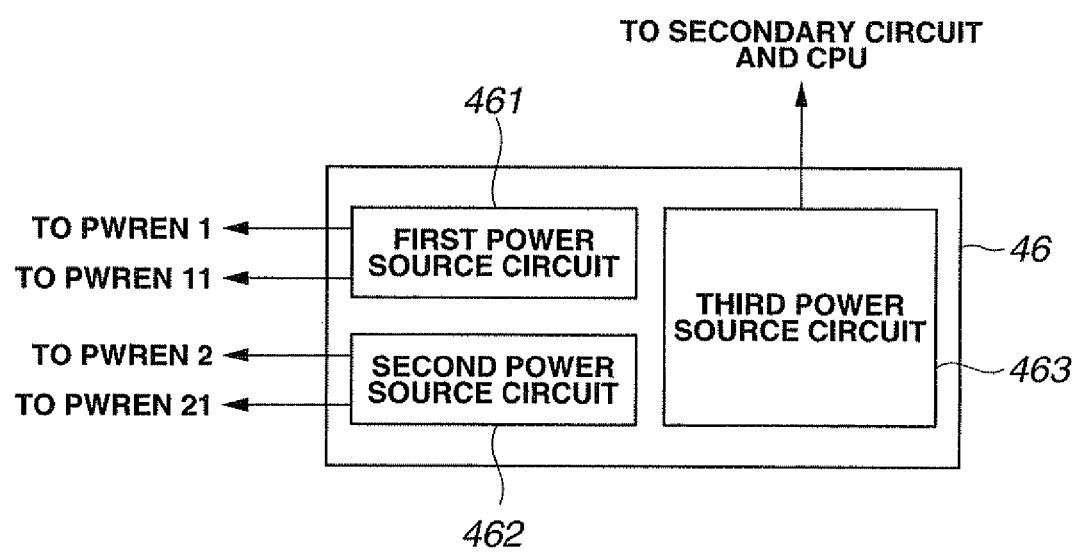
FIG. 2 is a view showing an example of a configuration of a power source portion included in the processor according to the present embodiment.
Figure 3:
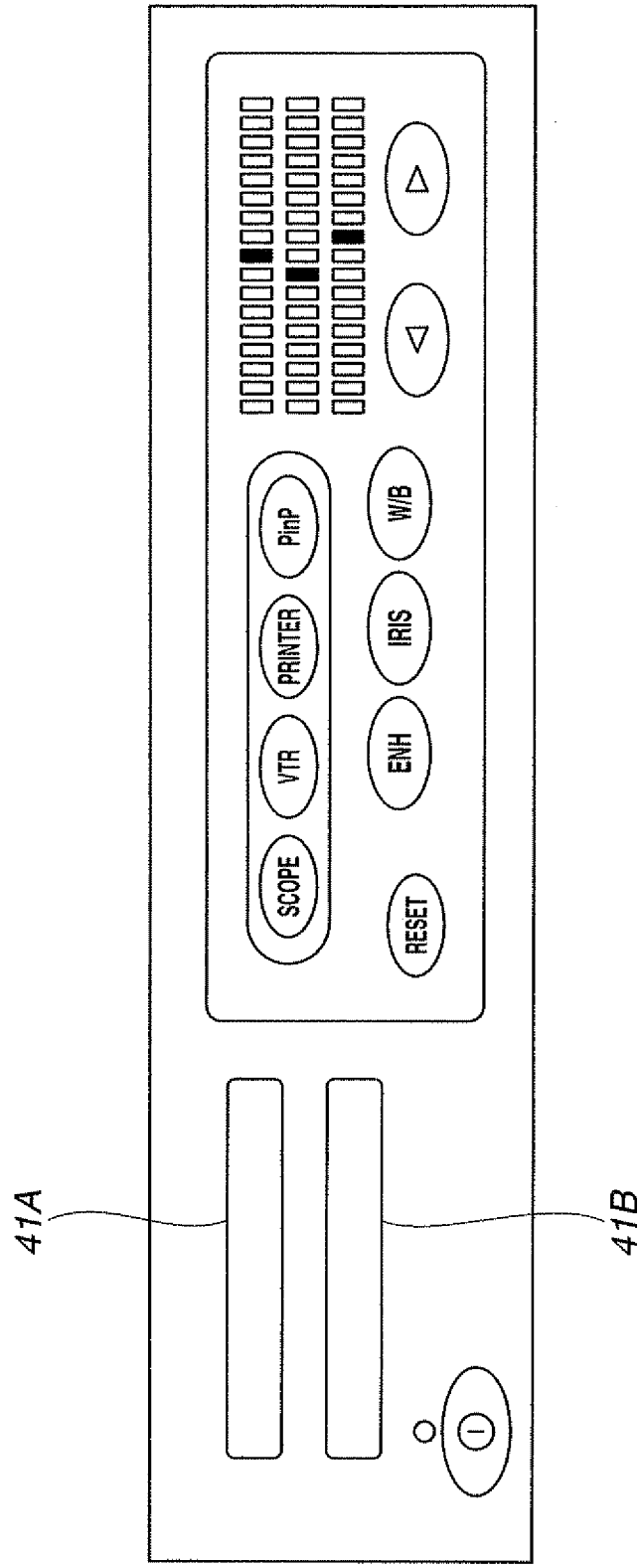
FIG. 3 is a view showing an example of a specific configuration of a front panel provided to the processor of FIG. 1.
Figure 4:
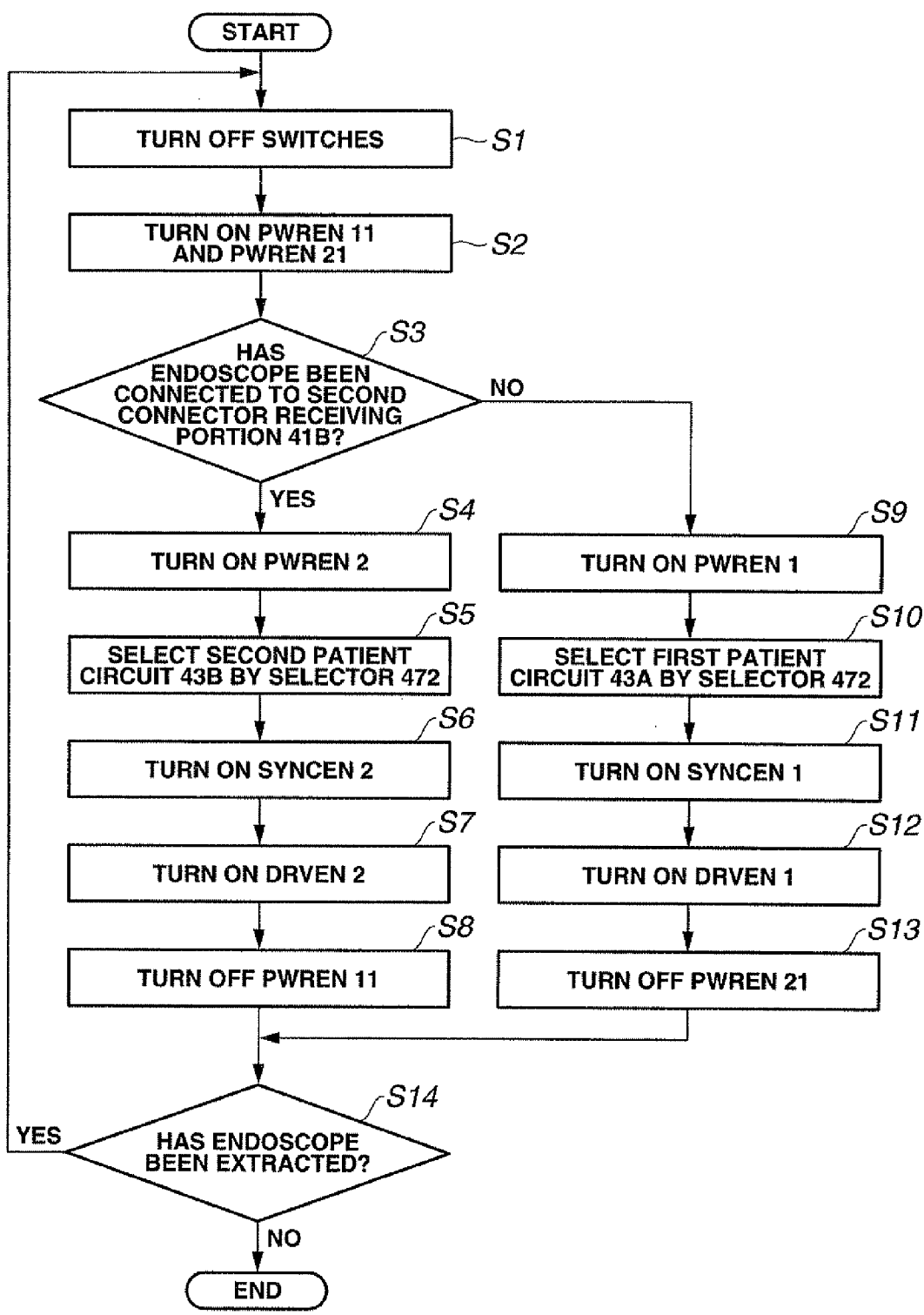
FIG. 4 is a flowchart showing an example of controls performed by the processor according to the present embodiment.

FIGS. 1 to 4 relate to the embodiment of the present invention. FIG. 1 is a view showing an example of a configuration of an endoscope system provided with a processor according to an embodiment of the present invention. FIG. 2 is a view showing an example of a configuration of a power source portion included in the processor according to the present embodiment. FIG. 3 is a view showing an example of a specific configuration of a front panel provided to the processor of FIG. 1. FIG. 4 is a flowchart showing an example of controls performed by the processor according to the present embodiment.

As shown in FIG. 1, an endoscope system 1 includes as an essential part: an endoscope 2 which is insertable into a body cavity and picks up an image of a subject in the body cavity to output the picked-up image as an image pickup signal; a light source device 3 which emits illumination light to illuminate a subject as an object to be picked up by the endoscope 2; a processor 4 which performs signal processing on an image pickup signal outputted from the endoscope 2 to output the processed image pickup signal as a video signal; and a monitor 5 which displays the image of the subject according to the video signal outputted from the processor 4.

As shown in FIG. 1, the endoscope 2 includes: an insertion portion 21 having a shape insertable into a body cavity; an objective optical system 22 and a CCD 23, which are provided at a distal end portion of the insertion portion 21; and a connector 24 which is provided at a proximal end portion of the insertion portion 21 and attachable/detachable to and from the processor 4. Furthermore, in the endoscope 2 is inserted a light guide 6, one end of which is connectable to a light guide receiving portion 31 of the light source device 3 and the other end of which is arranged at the distal end portion of the insertion portion 21. According to such a configuration, the illumination light emitted from the light source device 3 is transmitted by the light guide 6 connected to the light guide receiving portion 31, and thereafter emitted from the distal end portion of the insertion portion 21 to the subject.

The objective optical system 22 is arranged on a distal end surface of the distal end portion of the insertion portion 21 and forms an image of the subject.

The CCD 23 is arranged at an image-forming position of the objective optical system 22, and picks up the image of the subject formed by the objective optical system 22 to output the picked-up image as an image pickup signal.

As shown in FIG. 1, the processor 4 includes: a first connector receiving portion 41A and a second connector receiving portion 41B, to and from which the connector 24 of the endoscope 2 is attachable/detachable; a first connection detection portion 42A; a second connection detection portion 42B; a first patient circuit 43A; a second patient circuit 43B; insulation circuits 44A, 443, 44C, and 44D; a CPU 45; a power source portion 46 to which commercial power is supplied; and a secondary circuit 47.

The first connection detection portion 42A operates when a switch PWREN 11 is on, and detects a connecting state of the connector 24 to the first connector receiving portion 41A, to output a first connection detection signal when the connector 24 is connected to the first connector receiving portion 41A.

The second connection detection portion 42B operates when a switch PWREN 21 is on, and detects a connecting state of the connector 24 to the second connector receiving portion 41B, to output a second connection detection signal when the connector 24 is connected to the second connector receiving portion 41B.

The first and second connection detection signals are inputted to the CPU 45 after passing through the insulation circuit 44D.

The first patient circuit 43A is a circuit electrically connected to a post stage of the first connector receiving portion 41A, and includes a CCD driving portion 431A, an analog signal processing portion 432A, and an A/ID converter 433A. The first patient circuit 43A operates when the switch PWREN 1 and a switch SYNCEN 1 are on. Furthermore, the entirety of the first patient circuit 43A is connected to a GND 1 as a first reference potential point.

The CCD driving portion 431A outputs a driving signal to drive the CCD 23 in the endoscope 2 connected to the first connector receiving portion 41A. The driving signal is inputted to the CCD 23 after passing through the first connector receiving portion 41A and the connector 24, when a switch DRVEN 1 is on.

The analog signal processing portion 432A performs signal processing such as amplification and noise removal on an image pickup signal outputted from the endoscope 2 connected to the first connector receiving portion 41A, and thereafter outputs the image pickup signal subjected to the signal processing to the A/D converter 433A.

The A/D converter 433A converts the image pickup signal outputted from the analog signal processing portion 432A into a digital signal to output the digital signal. Then, the digital signal is inputted to the secondary circuit 47 after passing through the insulation circuit 44A.

The second patient circuit 43B is a circuit electrically connected to a post stage of the second connector receiving portion 41B, and includes a CCD driving portion 431B, an analog signal processing portion 432B, and an A/D converter 433B. The second patient circuit 43B operates when a switch PWREN 2 and a switch SYNCEN 2 are on. Furthermore, the entirety of the second patient circuit 43B is connected to a GND 2 as a second reference potential point different from the above-described first reference potential point. That is, the first patient circuit 43A and the second patient circuit 43B are provided in the processor 4 so as to be electrically independent of each other.

The CCD driving portion 431B outputs a driving signal to drive the CCD 23 in the endoscope 2 connected to the second connector receiving portion 41B. The driving signal is inputted to the CCD 23 after passing through the second connector receiving portion 41B and the connector 24, when a switch DRVEN 2 is on.

The analog signal processing portion 432B performs signal processing such as amplification and noise removal on an image pickup signal outputted from the endoscope 2 connected to the second connector receiving portion 41B, and thereafter outputs the image pickup signal subjected to the signal processing to the A/D converter 433B.

The A/D converter 433B converts the image pickup signal outputted from the analog signal processing portion 432B into a digital signal to output the digital signal. Then, the digital signal is inputted to the secondary circuit 47 after passing through the insulation circuit 44B.

The insulation circuit 44A has a configuration capable of outputting the digital signal from the A/D converter 433A to the secondary circuit 47, while electrically insulating between the first patient circuit 43A and the secondary circuit 47.

The insulation circuit 44B has a configuration capable of outputting the digital signal from the A/D converter 433B to the secondary circuit 47, while electrically insulating between the second patient circuit 43B and the secondary circuit 47.

The insulation circuit 44C has a configuration capable of outputting a synchronization signal from the secondary circuit 47 to the switch SYNCEN 1 connected to the first patient circuit 43A, while electrically insulating between the first patient circuit 43A and the secondary circuit 47. Furthermore, the insulation circuit 44C has, in addition to the above-described configuration, a configuration capable of outputting the synchronization signal from the secondary circuit 47 to the switch SYNCEN 2 connected to the second circuit 43B, while electrically insulating between the second patient circuit 43B and the secondary circuit 47.

The insulation circuit 44D has a configuration capable of mediating transmission and reception of various signals between the CPU 45 and the respective portions of the first connection detection portion 42A, the second connection detection portion 42B, the first patient circuit 43A and the second patient circuit 43B, while electrically insulating between the CPU 45 and the respective portions.

The CPU 45 performs a control to operate either the first patient circuit 43A or the second patient circuit 43B, based on the first connection detection signal and the second connection detection signal. Note that, the content of the control performed by the CPU 45 will be detailed later.

As shown in FIG. 2, the power source portion 46 includes: a first power source circuit 461 for supplying power required to operate the first connection detection portion 42A and the first patient circuit 43A; a second power source circuit 462 for supplying power required to operate the second connection detection portion 42B and the second patient circuit 43B; and a third power source circuit 463 for supplying power required to operate the CPU 45 and each of the portions in the secondary circuit 47.

Note that the first, second, and third power source circuits 461, 462, and 463 are provided in the power source portion 46 so as to be electrically independent of each other.

As shown in FIG. 1, the secondary circuit 47 includes: a timing generator 471; a selector 472; a digital signal processing portion 473; a mask generation portion 474 for generating and outputting a mask image, character information and the like; an image synthesizing portion 475; and a D/A converter 476. Note that, it is assumed that the entirety of the secondary circuit 47 of the present embodiment is connected to a reference potential point, a potential of which is different from both of the potential of the first reference potential point GND 1 to which the first patient circuit 43A is connected and the potential of the second reference potential point GND 2 to which the second patient circuit 43B is connected.

The timing generator 471 generates and outputs a synchronization signal related to the activation timing of the one patient circuit to be operated, of the first patient circuit 43A and the second patient circuit 43B.

When the first patient circuit 43A is operated, the selector 472 outputs to the digital signal processing portion 473 a digital signal inputted through the insulation circuit 44A, based on the control of the CPU 45. In addition, when the second patient circuit 43B is operated, the selector 472 outputs to the digital signal processing portion 473 a digital signal inputted through the insulation circuit 44B, based on the control of the CPU 45.

The digital signal processing portion 473 performs image processing such as γ-correction and image enhancement on the digital signal outputted from the selector 472, and thereafter outputs the digital signal subjected to the image processing to the image synthesizing portion 475.

The image synthesizing portion 475 synthesizes the digital signal outputted from the digital signal processing portion 473 and the mask image and the character information outputted from the mask generation portion 474, and outputs the synthesized digital signal and the mask image and the character information as a digital synthetic image signal to the D/A converter 476.

The D/A converter 476 converts the digital synthetic image signal outputted from the image synthesizing portion 475 into an analog video signal to output the analog video signal to the monitor 5. This allows the image in which the mask image and the character information is superimposed on the image of the subject picked up by the endoscope 2 to be displayed on the monitor 5.

Note that, it is assumed that the first connector receiving portion 41A and the second connector receiving portion 41B in the endoscope system 1 are arranged on the front panel of the processor 4 in a state shown in FIG. 3, for example.

In addition, the first connector receiving portion 41A and the second connector receiving portion 41B according to the present embodiment may be formed as a female type and include connecting terminals arranged at a position not directly touchable by a human body.

Next, a working of the endoscope system 1 according to the present embodiment will be described.

When the CPU 45 in the processor 4 included in the endoscope system 1 detects that a main power source has been turned on, the CPU 45 performs, as an initial setting, a control to turn off the switches, that is, the PWREN 1, PWREN 11, SYNCEN 1, DRVEN 1, PWREN 2, PWREN 21, SYNCEN 2, and DRVEN 2 (step S1 in FIG. 4).

After that, the CPU 45 turns on the switch PWREN 11 and the PWREN 21 among the above-mentioned switches, to operate the first connection detection portion 42A and the second connection detection portion 42B (step S2 in FIG. 4). This allows a connection detection signal to be outputted, the connection detection signal corresponding to either one of the first and the second connector receiving portions 41A, 41B, to which the endoscope 2 is connected.

The CPU 45 identifies whether the connection detection signal to be inputted is either the first connection detection signal or the second connection detection signal. When identifying that the connection detection signal to be inputted is the first connection detection signal, the CPU 45 determines that the endoscope 2 has been connected to the first connector receiving portion 41A. On the other hand, when identifying that the connection detection signal to be inputted is the second connection detection signal, the CPU 45 determines that the endoscope 2 has been connected to the second connector portion 41B.

When determining that the endoscope 2 has been connected to the second connector receiving portion 41B (step S3 in FIG. 4), the CPU 45 sequentially performs a control to turn on the switch PWREN 2 (step S4 in FIG. 4), a control to select the second patient circuit 43B by the selector 472 (step S5 in FIG. 4), a control to turn on the switch SYNCEN 2 (step S6 in FIG. 4), and a control to turn on the switch DRVEN 2 (step S7 in FIG. 4), and thereafter further performs a control to turn off the switch PWREN 11 (step S8 in FIG. 4).

That is, by performing the control in the step S8 in FIG. 4, the CPU 45 stops power supply to the first connection detection portion 42A corresponding to the first connector receiving portion 41A while the endoscope 2 is connected to the second connector portion 41B (while the second connection detection signal is inputted to the CPU 45).

In addition, after the steps S1 to S3 in FIG. 4, the controls in the steps S4 to S8 in FIG. 4 are performed. Thereby power is supplied to the second connection detection portion 42B and the second patient circuit 43B that are corresponding to the connector receiving portion 41B to which the endoscope 2 is connected, and power supply is stopped to the first connection detection portion 42A and the first patient circuit 43A that are corresponding to the connector receiving portion 41A to which the endoscope 2 is not connected.

On the other hand, when determining that the endoscope 2 has been connected to the first connector receiving portion 41A (step S3 in FIG. 4), the CPU 45 sequentially performs a control to turn on the switch PWREN 1 (step S9 in FIG. 4), a control to select the first patient circuit 43A by the selector 472 (step S10 in FIG. 4), a control to turn on the switch SYNCEN 1 (step S11 in FIG. 4), and a control to turn on the switch DRVEN 1 (step S12 in FIG. 4), and thereafter further performs a control to turn off the switch PWREN 21 (step S13 in FIG. 4).

That is, by performing the control in the step S13 in FIG. 4, the CPU 45 stops power supply to the second connection detection portion 42B corresponding to the second connector receiving portion 41B while the endoscope 2 is connected to the first connector receiving portion 41A (while the first connection detection signal is inputted to the CPU 45).

In addition, after the steps S1 to S3 in FIG. 4, the controls in the steps S9 to S13 in FIG. 4 are performed. Thereby power is supplied to the first connection detection portion 42A and the first patient circuit 43A that are corresponding to the connector receiving portion 41A to which the endoscope 2 is connected, and power supply is stopped to the second connection detection portion 42B and the second patient circuit 43B that are corresponding to the connector receiving portion 41B to which the endoscope 2 is not connected.

As described above, the processor 4 according to the present embodiment has a configuration and working in which the electrically independent patient circuits operate exclusively each other according to the connecting state of the endoscope 2 to the connector receiving portions.

After performing the above-described control in the step S8 or the step S13, for example based on whether or not the input of the connection detection signal to the CPU 45 is stopped, the CPU 45 determines whether or not the endoscope 2 is extracted from the first connector portion 41A or the second connector receiving portion 41B, (step S14 in FIG. 4). Unless the endoscope 2 is extracted from the first connector receiving portion 41A or the second connector receiving portion 41B, the CPU 45 terminates the series of controls while maintaining the state after the control in the steps S8 or the step S13 in FIG. 4 has been performed. When detecting that the endoscope 2 has been extracted from the first connector receiving portion 41A or the second connector receiving portion 41B, the CPU 45 repeatedly performs the series of controls from the step S1 in FIG. 4. That is, the CPU 45 restores the power supply to both of the first connection detection portion 42A and the second connection detection portion 42B in reaction to the extraction of the endoscope 2 from the first connector receiving portion 41B or the second connection detection portion 42B. This enables the user to smoothly perform, for example, the work to reattach the connector 24 of the endoscope 2 from the first connector receiving portion 41A to the second connector receiving portion 41B.

As described above, in the processor 4 according to the present embodiment, the patient circuits are provided so as to be electrically independent of each other and also the power source circuits corresponding to the patient circuits are provided so as to be electrically independent of each other. Furthermore, the processor 4 according to the present embodiment stops the power supply to the patient circuit corresponding to the connector receiving portion to which the endoscope is not connected, and supplies power only to the patient circuit corresponding to the connector receiving portion to which the endoscope is connected.

Since the processor 4 of the present embodiment has such a configuration and working, it is not necessary for the user to excessively aware of invasion of extraneous substance such as body fluid into the patient circuits. As a result, the burden on the user can be reduced, compared with a conventional processor.

Note that, it is needless to say that the present invention is not limited to the above described embodiment, and various modifications and applications are possible within the scope of the present invention.

What is claimed is:

1. An endoscope control apparatus comprising:
    a first connector receiving portion and a second connector receiving portion, to and from which an endoscope is attachable and detachable;
    a connection detection portion for detecting a connecting state of the endoscope in the first connector receiving portion and the second connector receiving portion and outputting a connection detection signal, the connection detection portion including a first connection detection portion for detecting a connecting state of the endoscope in the first connector receiving portion and a second connection detection portion for detecting a connecting state of the endoscope in the second connector receiving portion;
    a first patient circuit electrically connected to a post stage of the first connector receiving portion and connected also to a first reference potential point;
    a second patient circuit electrically connected to a post stage of the second connector receiving portion, and connected also to a second reference potential point, a potential of which is different from a potential of the first reference potential point, the second patient circuit being provided so as to be electrically independent of the first patient circuit; and
    a control portion configured to perform, based on the connection detection signal outputted from the connection detection portion, in a period from when the endoscope is connected to one connector receiving portion of the first connector receiving portion and the second connector receiving portion to when the endoscope is extracted from the one connector receiving portion, a control to carry out a power supply to one patient circuit and one connection detection portion which correspond to the one connector receiving portion and to stop a power supply to the other patient circuit and the other connection detection portion which correspond to the other connector receiving portion different from the one connector receiving portion, and when it is detected that the endoscope is extracted from the one connector receiving portion, a control to stop a power supply to the first patient circuit and the second patient circuit and to carry out a power supply to the first connection detection portion and the second connection detection portion.

2. The endoscope control apparatus according to claim 1, further comprising a secondary circuit disposed at a post stage of the first patient circuit and the second patient circuit, the secondary circuit being capable of receiving signals outputting from the first patient circuit and the second patient circuit in a state insulated from the first patient circuit and the second patient circuit,
    wherein the potential of the first reference potential point, the potential of the second reference potential point, and a potential of a third reference potential point connected to the secondary circuit are different from one another, and the first patient circuit, the second patient circuit, and the secondary circuit are provided so as to be electrically independent of one another.

3. The endoscope control apparatus according to claim 1, further comprising
    a first power source circuit for supplying power required to operate the first patient circuit and the first connection detection portion, and a second power source circuit for supplying power required to operate the second patient circuit and the second connection detection portion, wherein
    the first power source circuit and the second power source circuit are provided electrically independent of each other.

4. The endoscope control apparatus according to claim 1, further comprising
    a selector for connecting the one patient circuit of the first patient circuit and the second patient circuit to the secondary circuit based on the control by the control portion, the one patient circuit corresponding to the one connector receiving portion to which the endoscope is connected.

5. The endoscope control apparatus according to claim 1, wherein the control portion further performs a control to stop supply of a driving signal to be outputted to the other connector receiving portion, among driving signals for driving an image pickup device provided in the endoscope.

* * * * *